United States Patent
Sughrue et al.

(10) Patent No.: US 11,152,123 B1
(45) Date of Patent: Oct. 19, 2021

(54) PROCESSING BRAIN DATA USING AUTOENCODER NEURAL NETWORKS

(71) Applicant: Omniscient Neurotechnology Pty Limited, Sydney (AU)

(72) Inventors: Michael Edward Sughrue, Sydney (AU); Stephane Philippe Doyen, Glebe (AU); Peter James Nicholas, South Hurstville (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/145,240

(22) Filed: Jan. 8, 2021

(51) Int. Cl.
*G16H 50/70* (2018.01)
*G06N 3/08* (2006.01)
(Continued)

(52) U.S. Cl.
CPC .......... *G16H 50/70* (2018.01); *A61B 5/0044* (2013.01); *A61B 5/055* (2013.01); *G01R 33/4806* (2013.01); *G01R 33/56341* (2013.01); *G06N 3/088* (2013.01); *G16H 20/30* (2018.01); *G16H 40/67* (2018.01); *G16H 50/20* (2018.01);
(Continued)

(58) Field of Classification Search
CPC ........ G16H 20/30; G16H 30/20; G16H 30/40; G16H 40/67; G16H 50/20; G16H 50/30; G16H 50/70; G01B 33/4806; G01B 33/56341; G06N 3/088; A61B 5/0044; A61B 5/055; A61B 2576/026
See application file for complete search history.

(56) References Cited

U.S. PATENT DOCUMENTS 8,742,754 B2   6/2014   Hasan
9,747,421 B2   8/2017   Krishna et al.
(Continued)

FOREIGN PATENT DOCUMENTS

WO   WO 2001/038895   5/2001
WO   WO 2014/153466   9/2014
(Continued)

OTHER PUBLICATIONS

Baur C., Wiestler B., Albarqouni S., Navab N. Deep Autoencoding Models for Unsupervised Anomaly Segmentation in Brain MR Images. In: Crimi A., Bakas S., Kuijf H., Keyvan F., Reyes M., van Walsum T. (eds) Brainlesion: Glioma, Multiple Sclerosis, Stroke and Traumatic Brain Injuries. BrainLes 201 (Year: 2019).*

(Continued)

*Primary Examiner* — Fonya M Long
*Assistant Examiner* — Anthony Michael Balaj
(74) *Attorney, Agent, or Firm* — Fish & Richardson P.C.

(57) ABSTRACT

Methods, systems, and apparatus, including computer programs encoded on computer storage media, for processing brain data using autoencoder neural networks. One of the methods includes obtaining brain data captured by one or more sensors characterizing brain activity of a patient; processing the brain data to generate modified brain data that characterizes a predicted local effect of a future treatment on the brain of the patient; processing the modified brain data using an autoencoder neural network to generate reconstructed brain data; and determining, using the reconstructed brain data, a predicted global effect of the future treatment on the brain of the patient.

20 Claims, 8 Drawing Sheets

(51) Int. Cl.
  *G16H 40/67* (2018.01)
  *G16H 50/20* (2018.01)
  *G16H 50/30* (2018.01)
  *G16H 20/30* (2018.01)
  *A61B 5/055* (2006.01)
  *G01R 33/48* (2006.01)
  *G01R 33/563* (2006.01)
  *A61B 5/00* (2006.01)
  *G16H 30/20* (2018.01)
  *G16H 30/40* (2018.01)

(52) U.S. Cl.
  CPC ........ *G16H 50/30* (2018.01); *A61B 2576/026* (2013.01); *G16H 30/20* (2018.01); *G16H 30/40* (2018.01)

(56) References Cited

U.S. PATENT DOCUMENTS

| | | | |
|---|---|---|---|
| 2010/0004527 A1 | 1/2010 | Dale et al. | |
| 2017/0035320 A1 | 2/2017 | Verma et al. | |
| 2017/0052241 A1 | 2/2017 | Cetingul et al. | |
| 2018/0025489 A1 | 1/2018 | Tiwari et al. | |
| 2019/0102511 A1* | 4/2019 | Murray | G16B 20/00 |
| 2019/0320934 A1* | 10/2019 | Odry | G16H 40/20 |
| 2019/0371450 A1* | 12/2019 | Lou | G16H 50/30 |
| 2020/0020098 A1* | 1/2020 | Odry | G06K 9/6245 |
| 2020/0275838 A1* | 9/2020 | Javitt | A61N 2/006 |
| 2020/0352443 A1* | 11/2020 | Fox | A61B 5/0515 |

FOREIGN PATENT DOCUMENTS

| | | |
|---|---|---|
| WO | WO 2016/083927 | 1/2017 |
| WO | WO 2019/100032 | 5/2019 |

OTHER PUBLICATIONS

U.S. Appl. No. 16/920,078, filed Jul. 2, 2020, Sughrue et al..
Coalson et al.. "The impact of traditional neuroimaging methods on the spatial localization of cortical areas." Proceedings of the National Academy of Sciences, 2018, 115.27:E6356-65.
Dipy.org [online], "Introduction to Basic Tracking." retrieved on Dec. 2, 2020, retrieved from URL <https://dipy.org/documentation/1.3.0./examples_built/tracking_introduction_eudx/#example-tracking-introduction-eudx?>, 8 pages.
Huang et al.. "Inverse-Transform AutoEncoder for Anomaly Detection" arXiv, 2019, 5(6): 1-15.
LaPlante et al., "The Connectome Visualization Utility: Software for Visualization of Human Brain Networks," PLoS One, Dec. 2014, 9(( 12): 1-18.
Moreno-Donninguez, "Whole-brain Cortical Parcellation: A Hierarchical Method Based on dMRI Tractography" 2014, Ph.D. Thesis in Engineering, Max Planck Institute for Human Cognitive and Brain Sciences Leipzig, 188 pages.
Najdenovska et al.."In-vivo probabilistic atlas of human thalamic nuclei based on diffusion-weighted magnetic resonance imaging" Scientific Data, Nov. 2018, 5:180270.
Petrovic et al., "Evaluating Volumetric Brain Registration Performance Using Structural Connectivity Information", 2011, Med. Image Compuy Comput. Assist. Interv., 14(2):524-31.
Pypi.org, [online] "DeepDefacer: Automatic Removal of Facial Features via Deep Learning" Jan. 13, 2019, retrieved on Dec. 2, 2020, retrieved from URL <https://pypi.org/project/deepdefacer/>, 4 pages.
Toga et al.. "The role of image registration in brain mapping"; Image Vis Comput.. Jan. 2001, 19(1-2): 3-24.
Urchs et al., "MIST: A multi-resolution parcellation of functional brain networks," MNI Open Research, Dec. 5, 2017, 1(3):1-30.
Xia et al., "BrainNet Viewer: A Network Visualization Tool for Human Brain Connectomics," PLoS One, Jul. 2013, 8(7): 1-15.

* cited by examiner

PROCESSING BRAIN DATA USING AUTOENCODER NEURAL NETWORKS

CROSS-REFERENCE TO RELATED APPLICATIONS

This application is related to the U.S. patent application Ser. No. 17/066,171, filed on Oct. 8, 2020, and incorporated herein by reference in its entirety.

This application is also related to the U.S. patent application Ser. No. 17/066,178, filed on Oct. 8, 2020, and incorporated herein by reference in its entirety.

BACKGROUND

This specification relates to processing data related to the brain of a patient, e.g., functional magnetic resonance imaging (MRI) data and/or tractography data.

Brain functional connectivity data characterizes, for each of one or more pairs of locations within the brain of a patient, the degree to which brain activity in the pair of locations is correlated.

One can gather data related to the brain of the patient by obtaining and processing images of the brain of the patient, e.g., using magnetic resonance imaging (MM), diffusion tensor imaging (DTI), or functional MM imaging (fMRI). Diffusion tensor imaging uses magnetic resonance images to measure diffusion of water in a human brain. One can use the measured diffusion to generate tractography data, which can include images of neural tracts and corresponding white matter fibers of the subject brain.

Data related to the brain of a single patient can be highly complex and high-dimensional, and therefore difficult for a clinician to manually inspect and parse, e.g., to plan a surgery or diagnose the patient for a brain disease or mental disorder.

SUMMARY

This specification describes systems implemented as computer programs on one or more computers in one or more locations for processing brain data of a patient using an autoencoder neural network.

In this specification, an autoencoder neural network is a neural network that includes at least two subnetworks: an encoder subnetwork and a decoder subnetwork. The encoder subnetwork is configured to process a network input of the autoencoder and to generate an embedding of the network input. The decoder subnetwork is configured to process the embedding of the network input and to generate a reconstructed network input. Typically, an autoencoder neural network is trained to generate a reconstructed network input that is as similar to the network input as possible.

In some implementations described in this specification, a system can process "modified" brain data using an autoencoder neural network to generate reconstructed brain data. The modified brain data can characterize a predicted local effect of a future treatment on the brain of the patient, and the reconstructed brain data can characterize a global effect of the future treatment on the brain of the patient. Because a local effect of a treatment (i.e., an effect of the treatment on a region of the brain that is local to a target location of the treatment) can be easier to predict than the global effect of the treatment, the system can leverage the autoencoder neural network to generate an accurate prediction of the global effects of a treatment before the treatment is provided. The system can thus allow a user, e.g., a clinician or other medical professional, to determine a treatment for the patient that will be, or is more likely to be, safe and effective.

In some other implementations described in this specification, a system can process "desired" brain data using an inverted autoencoder neural network to generate "roadmap" brain data. The desired brain data can characterize a desired global effect of a future treatment on the brain of the patient, and the roadmap brain data can characterize a local effect of the future treatment on the brain of the patient. Because a local effect of a treatment can be easier to predict than the global effect of the treatment, the system can leverage the inverted autoencoder neural network to generate roadmap brain data from which a future treatment can be determined that, if provided to the patient, will actualize, or be more likely to actualize, the desired global effect of the future treatment. That is, the system or a user of the system, e.g., a clinician or other medical professional, can use the roadmap brain data to determine parameters of the future treatment (e.g., a location in the brain of the patient to target with the treatment) such that the future treatment will be, or is more likely to be, safe and effective.

In some other implementations described in this specification, a system can process brain data of a patient using an autoencoder neural network to generate reconstructed brain data, and then process the reconstructed brain data to determine whether the original brain data of the patient is anomalous, i.e., outside of a normal range of values. For example, the system can determine that the brain data is anomalous if a measure of the difference between the brain data and the reconstructed brain data exceeds a threshold. That is, the system can compare the original brain data to the reconstructed brain data (where the reconstructed brain data incorporates information from other patients learned during the training of the autoencoder neural network) to identify anomalies in the original brain data. In some such implementations, the system can further identify a subset of the original brain data that is anomalous, e.g., a subset corresponding to a particular region of the brain of the patient. The system can thus allow a user, e.g., a clinician or other medical professional, to quickly identify anomalies in the brain data that might indicate that the patient has a brain disease and, optionally, a region of the brain that might be the target for a treatment of the brain disease.

In this specification, brain data can be any data characterizing the brain of a patient. For example, brain data can include one or both of i) direct measurement data of the brain of the patient, e.g., images of the brain collected using brain imaging techniques, or ii) data that has been derived or generated from initial measurement data of the brain of the patient, e.g., correlation matrices.

Particular embodiments of the subject matter described in this specification can be implemented so as to realize one or more of the following advantages.

As described above, a set of brain data characterizing the brain of a single patient can often be incredibly large and complicated, and thus it can be difficult and time consuming for a user to extract useful information from the set of brain data. Using techniques described in this specification, a system can process brain data of a patient to generate a clinically-relevant network output that can be used by a user to provide safe and effective care for the patient. For example, the system can allow the user to determine a treatment for the patient significantly more accurately and significantly more efficiently (e.g., in less time or using fewer computational, memory, or network resources) than if the user manually reviewed the large corpus of brain data. More specifically, a correlation matrix, e.g., a correlation matrix of fMRI data, of the brain of a patient can be a matrix with more than a hundred elements, more than a thousand elements, or more typically more than a hundred thousand elements. When a set or series of such correlation matrices are being considered, a system for producing and/or analyzing such matrices may be processing more than a million elements. By using techniques described in this specification, a system can reduce the number of elements being considered by the user to produce clinically relevant data, e.g., a recommendation for a specific action, within 10 minutes, within 5 minutes, within 3 minutes, within a minute, within 30 seconds or within 5 seconds.

As described above, the long-term, global effects of a treatment on the brain of the patient can be very difficult to predict, even by experienced medical professionals. Using techniques described in this specification, a system can use training data representing the clinical outcomes of treatments provided to a large number of patients, e.g., more than a hundred, more than a thousand, more than a hundred thousand or more than a million patients, to train an autoencoder neural network to accurately predict the outcome of a particular treatment on the brain of a particular patient. Similarly, a system can use training data to train an autoencoder neural network to accurately characterize what treatment will produce, or is likely to produce, a desired outcome on the brain of the patient. The autoencoder neural networks described herein can thus learn complex, nonlinear relationships between different regions of the brain and different treatments thereof, allowing a user to pursue safe and effective treatments for a patient in a way that cannot be done by inspecting the brain data of the patient alone.

Using techniques described in this specification, a system can quickly identify one or more regions, e.g., parcellations, in the brain of the patient whose brain data is outside a normal range, and therefore might be an indicator of a brain disease. The system can then display data characterizing the identified regions to the user, so that the user is not forced to search through and analyze a large amount of data that is not clinically relevant. Therefore, the amount of time that a user must spend to discover the portion of the brain data that is useful to the user can be drastically reduced, resulting in improved outcomes for patients, users and/or clinicians, especially when effective care requires time sensitive investigations.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a system that can brain data of a patient using an autoencoder neural network.

Figure 1A:
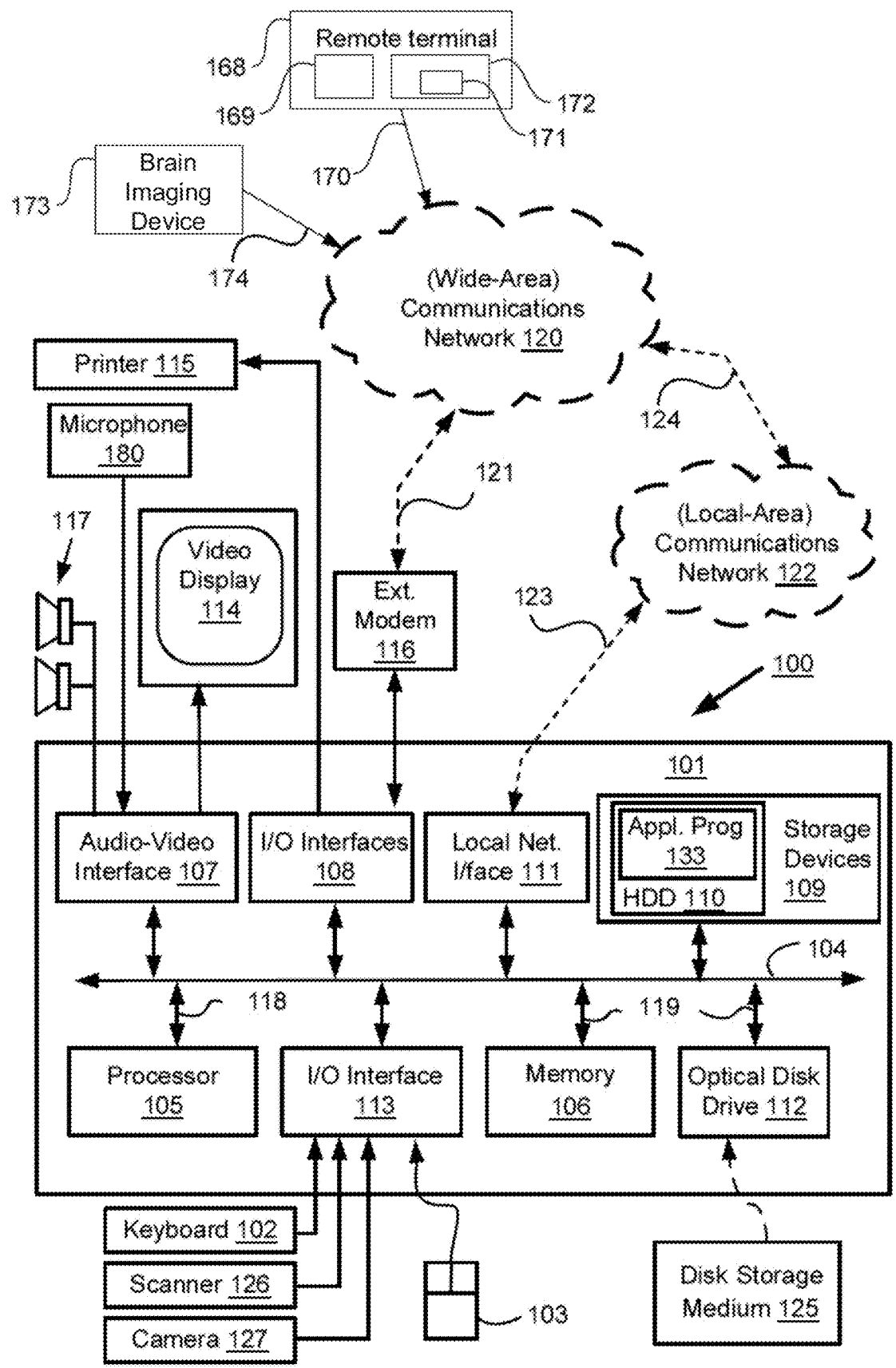
FIG. 1A and FIG. 1B are block diagrams that illustrate an example computer system for use in processing medical images.
Figure 1B:
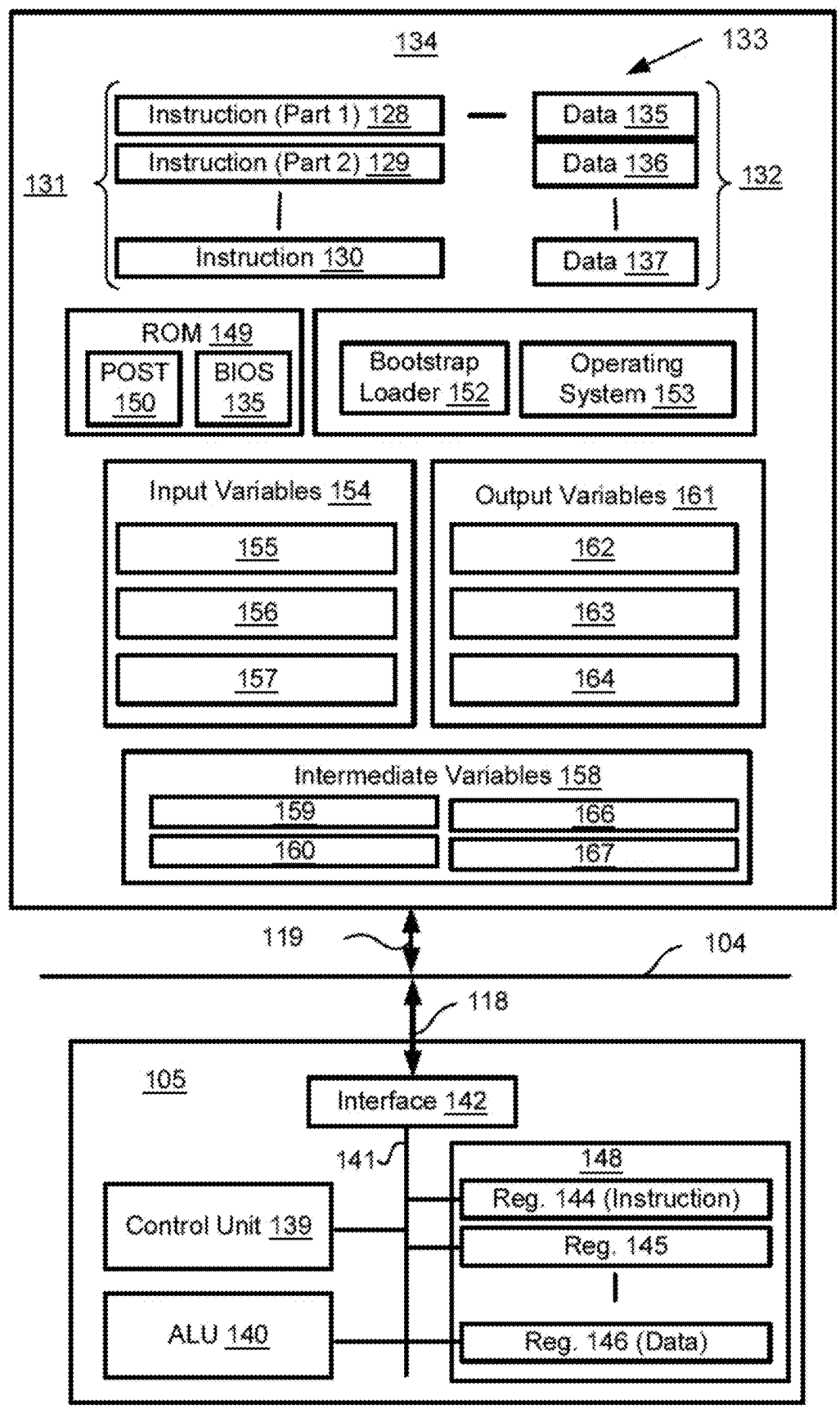

FIGS. 1A and 1B are block diagrams of a general-purpose computer system 100 upon which one can practice arrangements described in this specification. The following description is directed primarily to a computer server module 101. However, the description applies equally or equivalently to one or more remote terminals 168.

As seen in FIG. 1A, the computer system 100 includes: the server computer module 101; input devices such as a keyboard 102, a pointer device 103 (e.g., a mouse), a scanner 126, a camera 127, and a microphone 180; and output devices including a printer 115, a display device 114 and loudspeakers 117. An external Modulator-Demodulator (Modem) transceiver device 116 may be used by the computer server module 101 for communicating to and from the remote terminal 168 over a computer communications network 120 via a connection 121 and a connection 170. The aforementioned communication can take place between the remote terminal 168 and "the cloud" which in the present description comprises at least the one server module 101. The remote terminal 168 typically has input and output devices (not shown) which are similar to those described in regard to the server module 101. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer server module 101 typically includes at least one processor unit 105, and a memory unit 106. For example, the memory unit 106 may have semiconductor random access memory (RAM) and semiconductor read only memory (ROM). The remote terminal 168 typically includes as least one processor 169 and a memory 172. The computer server module 101 also includes a number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may include an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial or parallel connectivity; the former may be implemented according to the Universal Serial Bus (USB) standards and having corresponding USB connectors (not illustrated). Storage memory devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119.

The techniques described in this specification may be implemented using the computer system 100, e.g., may be implemented as one or more software application programs 133 executable within the computer system 100. In some implementations, the one or more software application programs 133 execute on the computer server module 101 (the remote terminal 168 may also perform processing jointly with the computer server module 101), and a browser 171 executes on the processor 169 in the remote terminal, thereby enabling a user of the remote terminal 168 to access the software application programs 133 executing on the server 101 (which is often referred to as "the cloud") using the browser 171. In particular, the techniques described in this specification may be effected by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules performs the described techniques and a second part and the corresponding code modules manage a user interface between the first part and the user.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product. Software modules for that execute techniques described in this specification may also be distributed using a Web browser.

The software 133 is typically stored in the HDD 110 or the memory 106 (and possibly at least to some extent in the memory 172 of the remote terminal 168). The software is loaded into the computer system 100 from a computer readable medium, and executed by the computer system 100. Thus, for example, the software 133, which can include one or more programs, may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. For example, through manipulation of the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 can execute. The POST program 150 can be stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 can activate the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high-level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source 173, e.g., a brain imaging device 173 such such as an Mill or DTI scanner, across one of the networks 120, 122, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

Some techniques described in this specification use input variables 154, e.g., data sets characterizing the brain of a patient, which are stored in the memory 134 in corresponding memory locations 155, 156, 157. The techniques can produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle can include i) a fetch operation, which fetches or reads an instruction 131 from a memory location 128, 129, 130; ii) a decode operation in which the control unit 139 determines which instruction has been fetched; and iii) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the techniques described in this specification may be associated with one or more segments of the program 133 and is performed by the register section 144, 145, 146, the ALU 140, and the control unit 139 in the processor 105 working together to perform the fetch, decode, and execute cycles for every instruction in the instruction set for the noted segments of the program 133. Although a cloud-based platform has been described for practicing the techniques described in this specification, other platform configurations can also be used. Furthermore, other hardware/software configurations and distributions can also be used for practicing the techniques described in this specification.

Figure 2A:
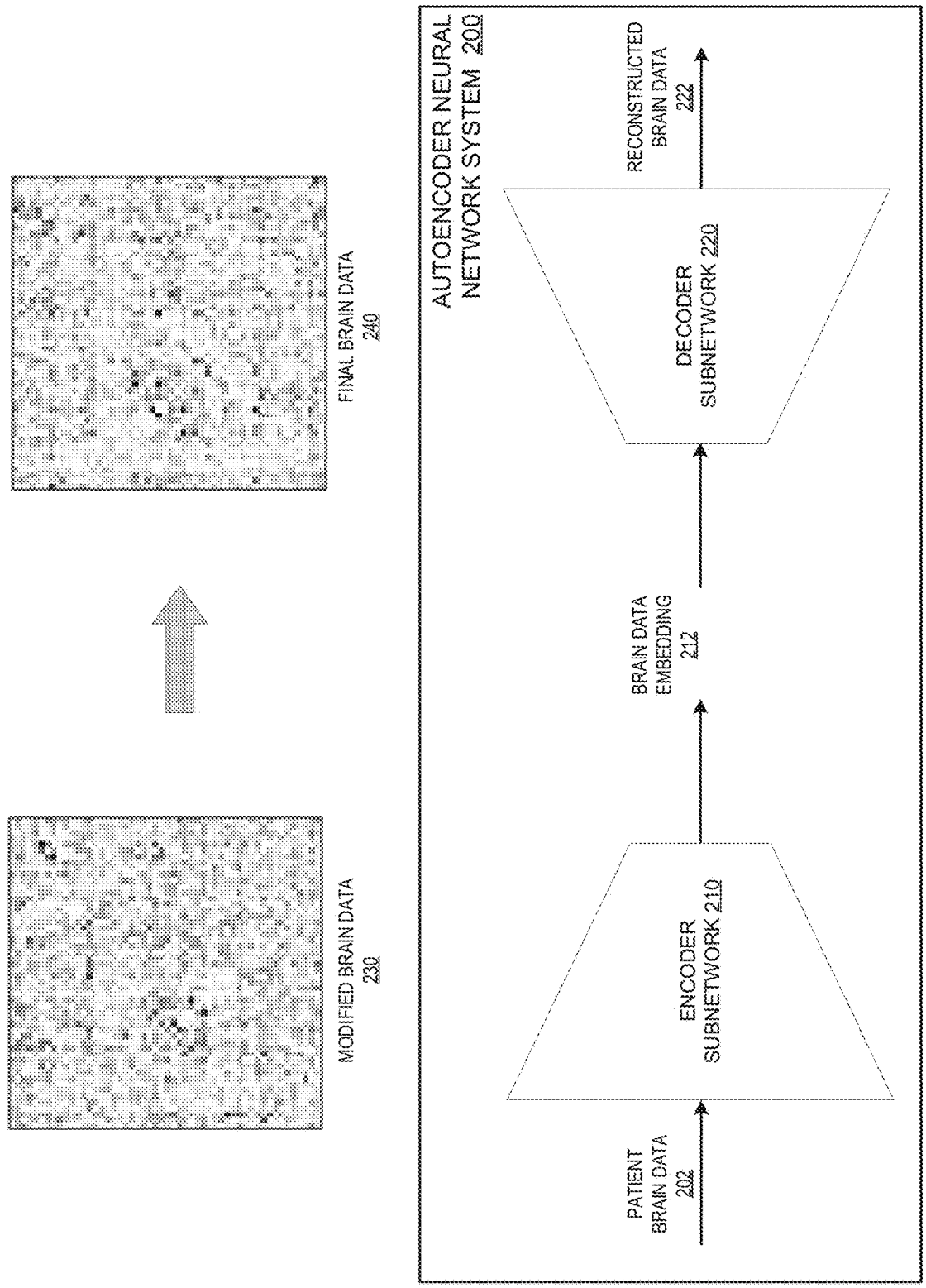
FIG. 2A is a diagram of an example autoencoder neural network system.

FIG. 2A is a diagram of example autoencoder neural network system 200. The autoencoder neural network system 200 is an example of systems implemented as computer programs on one or more computers in one or more locations, in which the systems, components, and techniques described below can be implemented.

The autoencoder neural network system 200 is configured to process patient brain data 202 and to generate reconstructed patient brain data 222 corresponding to the patient brain data 202.

The autoencoder neural network system 200 includes an encoder subnetwork 210 and a decoder subnetwork 220. The encoder subnetwork 210 is configured to process the brain data 202 and to generate an embedding 212 of the brain data 202. The decoder subnetwork 220 is configured to process the embedding 212 of the brain data 202 and to generate the reconstructed brain data 222. In this specification, an embedding is an ordered collection of numeric values that represents an input in a particular embedding space; e.g., an embedding can be a vector of floating point or other numeric values that has a fixed dimensionality. In this specification, reconstructed brain data is brain data that has been estimated using an embedding of the brain data, e.g., by processing the embedding using a decoder subnetwork of an autoencoder neural network.

Generally, the embedding 212 has a lower dimensionality than the brain data 202, while the reconstructed brain data 222 has the same dimensionality as the patient brain data 202. For example, the dimensionality of the embedding 212 can be $\frac{1}{10}^{th}$, $\frac{1}{100}^{th}$, or $\frac{1}{1000}^{th}$ the size of the dimensionality of the brain data 202. That is, there is a loss of information when the brain data 202 is processed by the encoder subnetwork 210 to generate the embedding 212, and so the reconstructed brain data 222 is only an approximation of the original brain data 202. During training, the encoder subnetwork 202 can learn to encode as much information from the brain data 202 as possible into the embedding 212, and the decoder subnetwork 220 can learn to reconstruct the brain data 202 to generate the reconstructed brain data 222 such that the reconstructed brain data 222 reflects the information encoded into the embedding 212.

That is, the autoencoder neural network system 200 can be configured through training to generate reconstructed patient brain data 222 such that a difference between the patient brain data 202 and the reconstructed patient brain data 202 is reduced below a threshold or minimized. For example, a training system can process training examples that each include brain data corresponding to respective different patients using the autoencoder neural network system 200 to generate respective sets of reconstructed brain data. For each training example, the training system can determine a reconstruction error that characterizes a difference between i) the brain data of the respective patient and ii) the corresponding reconstructed brain data. For example, the reconstruction error can be the $L_1$ or $L_2$ distance between the brain data and the reconstructed brain data, or squared versions thereof. As another example, the reconstruction error can be the root mean squared error between the brain data and the reconstructed brain data.

The training system can then backpropagate the reconstruction error through the autoencoder neural network system 200 to determine an update to the values of the parameters of the autoencoder neural network system 200, e.g., using gradient descent. For example, the training system can determine an update to the values of the parameters of both the encoder subnetwork 210 and the decoder subnetwork 220 (i.e., the encoder subnetwork 210 and the decoder subnetwork 220 can be trained concurrently). In other words, the training system can train the autoencoder neural network system 200 in an unsupervised manner, i.e., using training examples that do not include a ground-truth signal, e.g., a ground-truth embedding 212 of the brain data of the training example.

The brain data 202 can include any data characterizing the brain of the patient. For example, the brain data 202 can include one or more of blood-oxygen-level-dependent imaging data, fMRI data, or EEG data captured from the brain of the patient. Instead or in addition, the brain data 202 can include data that has been generated using respective raw data captured from the brain of the patient. For example, the brain data 202 can include correlation data that characterizes, for each pair of regions in the brain of the patient, a degree of correlation between the respective brain activity of the regions in the brain of the patient. As a particular example, each region can be a parcellation in the brain of the patient, as defined by a brain atlas.

In this specification, a parcellation is a predefined region of the brain. For example, a parcellation can be defined by boundaries on a three-dimensional volume of the brain. A parcellation can be defined such that the neurons in the parcellation are functionally similar according to one or more criteria. For example, a set of parcellations can be defined according to changes in cortical architecture, function, connectivity, and/or topography.

In this specification, a brain atlas is data that defines one or more parcellations of a brain of a patient, e.g., by defining in a common three-dimensional coordinate system the coordinates of the outline of the parcellation or the volume of the parcellation. As another example, the brain data 202 can include tractography data that characterizes neural tracts connecting pairs of regions in the brain of the patient, e.g., pairs of parcellations in the brain of the patient.

In some implementations, the autoencoder neural network system 200 can simulate the effect of treatment on the brain of the patient.

For example, the autoencoder neural network system 200 can obtain modified brain data 230 that characterizes a predicted local effect of a future treatment on the brain of the patient. That is, the modified brain data 230 has been generated by modifying real brain data captured from the brain of the patient in order to reflect the predicted local effect of the future treatment. In this specification, a local effect of a treatment is an effect that is local to a target location of the treatment. For example, the local effect of a treatment can be the effect of the treatment on the parcellation in the brain of the patient at which the treatment is targeted. As another example, the local effect of a treatment can be the effect of the treatment on the region of the brain within a threshold distance of the location at which the treatment is targeted, e.g., within a millimeter or a centimeter of the target location.

A system (e.g., the autoencoder neural network system 200 or an external system) can generate the modified brain data 230 by identifying a target location in the brain of the patient, and modifying the brain data of the patient corresponding to the target location, and optionally one or more neighboring locations to the target location. The system can modify the brain data corresponding to the target location according to how the future treatment is expected to modify the brain data, according to the parameters of the future treatment. As a particular example, the system can modify the values in a set of correlation data (e.g., as represented by a correlation matrix in FIG. 2A) corresponding to the particular parcellation that is the target of the treatment, e.g., by either increasing or decreasing the identified correlation between the brain activity in the particular parcellation and the brain activity in one or more other parcellations in the brain of the patient.

The future treatment can be any appropriate treatment on the brain of the patient. For example, the future treatment can be a drug therapy that may be provided to the patient and that targets a particular location in the brain of the patient. As another example, the future treatment can be a surgery on the target location in the brain of the patient. As another example, the future treatment can be transcranial magnetic stimulation (TMS) targeted at the target location in the brain of the patient.

The autoencoder neural network system 200 can process the modified brain data 230 to generate final brain data 240. In particular, the autoencoder neural network system 200 can i) process the modified brain data 230 using the encoder subnetwork 210 to generate an embedding of the modified brain data 230, and ii) process the embedding of the modified brain data 230 using the decoder subnetwork 220 to generate the final brain data 240.

The final brain data 240 characterizes a predicted global effect of the future treatment on the brain of the patient. In this specification, a global effect of a treatment is an effect of the treatment on one or more locations in the brain of the patient that are not local to a target location of the treatment. For example, the global effect of a treatment can be the effect of the treatment on the entire brain of the patient. As another example, the global effect of a treatment can be the effect of the treatment on one or more neighboring locations of the target location in the brain of the patient, e.g., one or more neighboring parcellations of the target parcellation.

In other words, a local effect of a treatment can be any effect by which an intervention on a specific parcellation in the brain of the patient directly affects the functioning of the specific parcellation. A global effect of the treatment can characterize how the treatment changes the functioning of one or more networks of parcellations in the brain of the patient.

As a particular example, if the modified brain data 230 includes modified correlation data as described above, then the final brain data 240 can include correlation data that reflects, for one or more particular parcellations that were not the target parcellation of the treatment (e.g., for every parcellation in the brain of the patient), how the treatment will affect the correlation between the brain activity in the particular parcellation and the brain activity in one or more other parcellations in the brain of the patient.

The output of the autoencoder neural network system 200 can represent the global effect of the future treatment because of how the autoencoder neural network system 200 has been trained. During training, the autoencoder neural network system 200 receives brain data 202 corresponding to untreated patients, i.e., patients who have not recently undergone brain treatments and whose brain data 202 therefore does not reflect the local effects of a treatment. The encoder subnetwork 210 learns to encode the most useful information in the brain data 202 into the brain data embeddings 212. The decoder subnetwork 210 learns to generate, using the brain data embeddings 212, reconstructed brain data 222 that imitates the structure of the brain data 202 of these untreated patients. Therefore, when provided modified brain data 230 that does reflect a local effect of a treatment, e.g., the effect immediately after the treatment is provided, the encoder subnetwork 210 can generate an embedding that encodes the information from the local effect in the target location of the treatment. The decoder subnetwork 220 can then generate reconstructed brain data 240 that imitates brain data that i) includes the local effect in the target location of the treatment and ii) corresponds to an untreated patient. That is, the final brain data 240 reflects how the rest of the brain data outside of the target location would be structured for an untreated patient, given that the local effect is present in the target location, i.e., how the local effect might propagate to the rest of the brain data.

The final brain data 240 can be used to determine what the global effect of the future treatment will be if the treatment is provided to the brain of the patient, e.g., whether the future treatment will be safe and/or effective. For example, a user of the autoencoder neural network system 200 can analyze the final brain data 240 to determine whether the future treatment should be provided to the patient. As another example, the final brain data 240 can be processed by an anomaly detection engine, e.g., the anomaly detection engine 330 depicted in FIG. 3, to determine whether the final brain data 240 is anomalous. That is, the anomaly detection engine can determine whether providing the treatment will cause one or more anomalies in the brain of the patient. This process is described in more detail below with reference to FIG. 3.

In some cases, the local effect of the future treatment on the brain of the patient might reflect a short-term effect of the future treatment, e.g., the effect of the treatment within seconds, minutes, hours, or days after the treatment has been provided to the brain of the patient. The global effect of the future treatment on the brain of the patient might reflect the long-term effect of the future treatment, e.g., the effect of the treatment days, weeks, months, or years after the treatment has been provided to the brain of the patient. Thus, a user can use the autoencoder neural network 200 to predict the long-term effect of the future treatment, in an effort to ensure the safety and efficacy of the treatment.

In some implementations, the autoencoder neural network system 200 can process multiple different sets of modified brain data 230, each corresponding to a respective different future treatment to generate respective sets of final brain data 240. Each future treatment can have different parameters, e.g., different strengths, different doses, different schedules, or different target locations. An external system can then help determine, from the respective sets of final brain data 240, which future treatments will be, or will likely be, the most safe and/or effective according to the reconstructed brain data, and therefore which future treatment a clinician should consider recommending be provided to the patient.

As a particular example, a system can process multiple different sets of modified brain data 230 using the autoencoder neural network system 200 in an attempt to generate a particular set of "desired" brain data. That is, the system processes the multiple different sets of modified brain data 230, generating a respective set of final brain data 240 for each set of modified brain data 230, in order to identify a particular set of modified brain data 230 whose corresponding set of final brain data 240 matches, or is closest to matching, the set of desired brain data. Thus, the particular set of modified brain data 230 represents the local effect of a treatment whose global effect is the set of desired brain data. For example, the system can use a "brute force" approach to identifying the particular set of modified brain data 230; that is, the system can systematically process many different sets of modified brain data 230 (e.g., using a grid search) until identifying the particular set of modified brain data 230.

As another example, the system can determine an initial set of modified brain data 230 and process the initial set of modified brain data using the autoencoder neural network system 200. The system can determine a difference between i) the final brain data 240 generated using the initial set of modified brain data 230 and ii) the desired brain data. The system can then backpropagate the difference through the autoencoder neural network system 200 in order to generate an update to the initial modified brain data 230 that will decrease the error. That is, instead of updating the parameters of the neural network system 200 during the backpropagation, the system updates the input to the autoencoder neural network system 200, generating a new set of modified brain data 230. The system can then process the new set of modified brain data 230 using the autoencoder neural network system 200 and determine another update to the input that will further decrease the difference, i.e., that will cause the corresponding final brain data 240 to be even closer to the desired brain data. The system can iteratively repeat this process until identifying the particular set of modified brain data that generates the desired brain data. For example, the system can perform a predetermined number of iterations, or repeat the process until a difference between the generated final brain data 240 and the desired brain data falls below a predetermined threshold.

In some implementations, the system can perform the above iterative process multiple times with different "seed" initial sets of modified brain data 230, and, after completing each iterative process, select the particular modified set of brain data that generates final brain data 240 that is closest to the desired brain data.

Other example techniques for determining a set of modified brain data that will, or is likely to, effectuate a particular desired result in the brain of the patient are discussed below with reference to FIG. 2B.

Figure 2B:
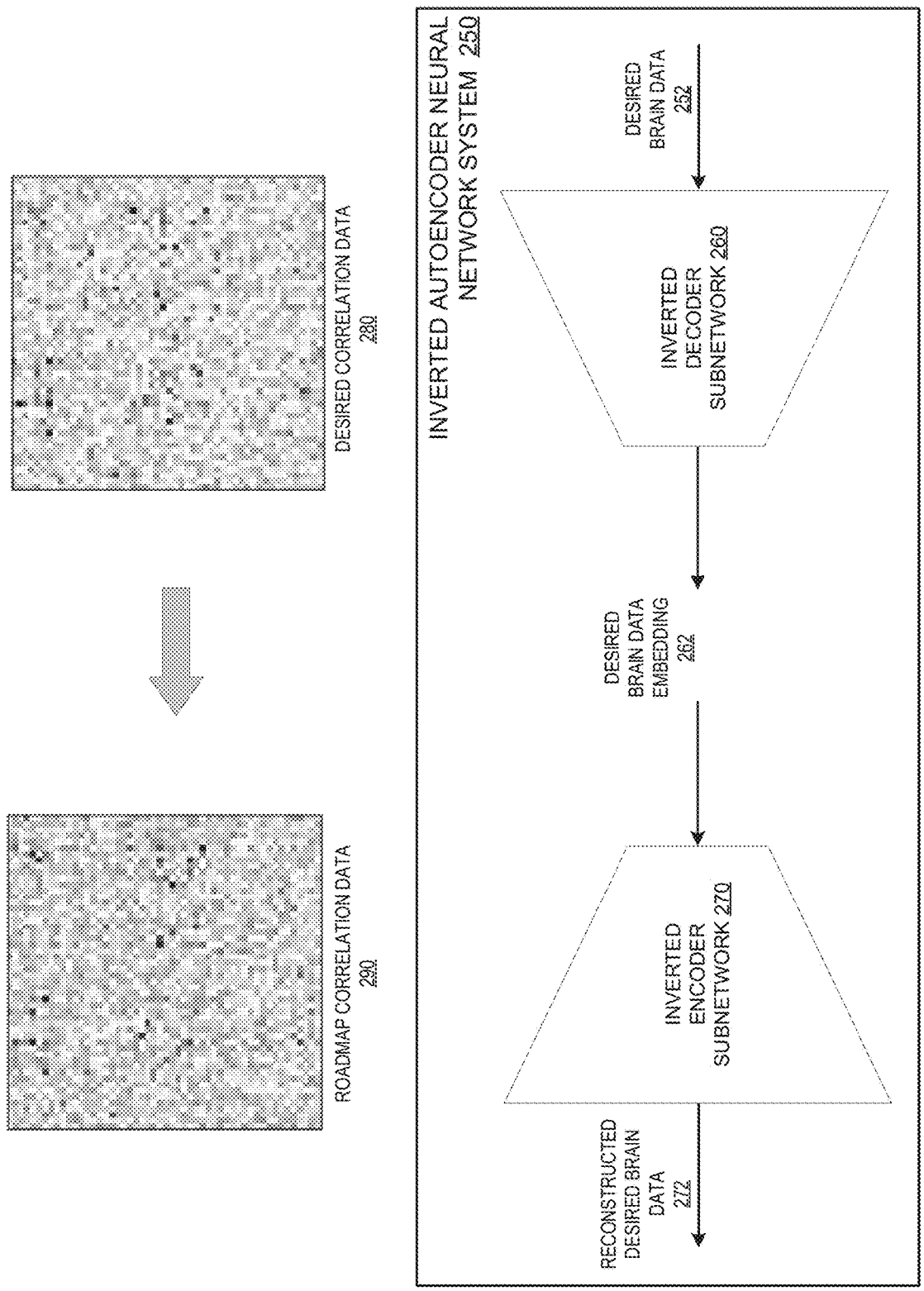
FIG. 2B is a diagram of an example inverted autoencoder neural network system.

FIG. 2B is a diagram of example inverted autoencoder neural network system 250. The inverted autoencoder neural network system 250 is an example of systems implemented as computer programs on one or more computers in one or more locations, in which the systems, components, and techniques described below can be implemented.

The inverted autoencoder neural network system 250 is an inverted version of the autoencoder neural network 200 depicted in FIG. 2A. In this specification, an inverted neural network is a neural network that inverts one or more operations of a subject neural network such that the inverted neural network maps the outputs of the subject neural network to the inputs of the subject neural network. Similarly to the autoencoder neural network system 200 depicted in FIG. 2A, the inverted autoencoder neural network system 250 is configured to process brain data to generate reconstructed brain data.

The autoencoder neural network system includes an inverted decoder subnetwork 260 and an inverted encoder subnetwork 270. The inverted decoder subnetwork 260 is configured to process the brain data to generate an embedding of the brain data, and the inverted encoder subnetwork 270 is configured to process the embedding of the brain data to generate reconstructed brain data. The inverted decoder subnetwork 260 can be an inverted version of the decoder subnetwork 220 depicted in FIG. 2A. Similarly, the inverted encoder subnetwork 270 can be an inverted version of the encoder subnetwork 210 depicted in FIG. 2A.

The inverted autoencoder neural network system 250 can be determined using the autoencoder neural network system 200, after the autoencoder neural network system 200 has been trained.

The architecture of the inverted autoencoder neural network system 250 can be the inverse of the architecture of the autoencoder neural network system 200. If the autoencoder neural network system 200 has N neural network layers, then the inverted autoencoder neural network system 250 can also have N neural network layers, where the $i^{th}$ neural network layer of the inverted autoencoder neural network system 250 corresponds to the $(N-i+1)^{th}$ neural network layer of the autoencoder neural network system 200. The architecture of the $i^{th}$ neural network layer of the inverted autoencoder neural network system 250 can be an inverted version of the architecture of the $(N-i+1)^{th}$ neural network layer of the autoencoder neural network system 200. That is, if the $(N-i+1)^{th}$ neural network layer of the autoencoder neural network system 200 receives a layer input of a first dimensionality (e.g., $L_i \times W_i \times H_i$) and generates a layer output of a second dimensionality (e.g., $L_o \times W_o \times H_o$), then the $i^{th}$ neural network layer of the inverted autoencoder neural network system 250 receives a layer input of the second dimensionality and generates a layer output of the first dimensionality.

The parameter values of the inverted autoencoder neural network system 250 can be determined using the trained parameter values of the autoencoder neural network system 200, by any appropriate process.

In some implementations, the inverted autoencoder neural network system 250 can be used to identify a treatment that, if provided to a patient, would effect a particular desired outcome on the brain of the patient.

For example, the inverted autoencoder neural network system 250 can obtain desired brain data 252 that characterizes a desired global effect of a future treatment on the brain of a patient. That is, the desired brain data 252 represents a desired state of the brain of the patient after the treatment has been provided to the patient.

In some implementations, a system (e.g., the inverted autoencoder neural network system 250 or an external system) can determine the desired brain data 252 of the patient using brain data corresponding to a different second patient that reflect the desired global effect of the future treatment. For example, the desired brain data 252 can be the same as the brain data of the second patient. As another example, the desired brain data 252 can be generated by combining i) current brain data of the patient (i.e., before the treatment is provided to the patient) and ii) brain data of the second patient.

In some other implementations, the system can determine the desired brain data 252 of the patient using only the current brain data of the patient, i.e., by modifying some or all of the elements of the current brain data of the patient to reflect the desired outcome.

The inverted autoencoder neural network system 250 can process the desired brain data 252 to generate reconstructed desired brain data 272. In particular, the inverted autoencoder neural network system 250 can i) process the desired brain data 252 using the inverted decoder subnetwork 260 to generate an embedding 262 of the desire brain data 252, and ii) process the embedding 262 of the desire brain data 252 using the inverted encoder subnetwork 270 to generate reconstructed desired brain data 272.

The reconstructed desired brain data 272 can characterize a predicted local effect of the future treatment on the brain of the patient. That is, the reconstructed desired brain data 272 can reflect the predicted effect of the treatment, e.g., the short-term effect of the treatment, on the location at which the treatment will be targeted.

The reconstructed desired brain data 272 can be used to determine parameters of the future treatment such that the future treatment will actualize the desired global effect reflected in the desired brain data 252. For example, the reconstructed desired brain data 272 can be used to determine a recommended location in the brain of the patient to target with the future treatment. As another example, the reconstructed desired brain data 272 can be used to determine a recommended strength or dose of the future treatment. As another example, the reconstructed desired brain data 272 can be used to determine a recommended schedule for providing the future treatment to the patient.

For example, an external system can identify one or more differences between i) the reconstructed desired brain data 272 and ii) the current brain data of the patient. As a particular example, the external system can identify one or more elements in the reconstructed desired brain data 272 that have the largest difference between the corresponding elements of the current brain data of the patient. The external system can then recommend the target location of the future treatment to be a location in the brain of the patient corresponding to the one or more determined differences. Instead or in addition, the external system can recommend a strength or dose of the future treatment according to a magnitude of the one or more determined differences.

Thus, the reconstructed desired brain data 172 can also be called "roadmap" brain data because the reconstructed desired brain data 172 can be used as a roadmap to determine a future treatment that, if provided to the patient, will, or will likely, actualize the desired global effect.

As a particular example, the desired brain data 252 can include desired correlation data 280 (e.g., as represented by a correlation matrix in FIG. 2B) that includes, for each of one or more pairs of parcellations in the brain of the patient, a desired correlation between the respective brain activity in the pair of parcellations. The inverted autoencoder neural network system 250 can process the desired correlation data 280 to generate roadmap correlation data 290 (e.g., as represented by a correlation matrix in FIG. 2B) that includes, for each of the one or more pairs of parcellations in the brain of the patient, a "roadmap" correlation between the respective brain activity in the pair of parcellations. The external system can then identify a difference between the desired correlation data 280 and the current brain data of the patient in order to determine the parameters of a future treatment. For example, the external system can identify a particular parcellation whose correlation values are different between the desired correlation data 280 and the current brain data of the patient, and determine the parameters of a TMS treatment that will stimulate the particular parcellation.

The output of the inverted autoencoder neural network system 250 can represent the local effect of the future treatment because of the training of the autoencoder neural network 200, i.e., the network that was used to determine the inverted autoencoder neural network system 250. As described above, the autoencoder neural network 200 can be configured through training to learn the relationships between different portions of the input brain data 202 (e.g., relationships between the brain data 202 corresponding to respective parcellations in the brain of the patient). Therefore, inverting the autoencoder neural network system 200 can configure the inverted decoder subnetwork 260 to process input brain data 252 to generate embeddings 262 that encode the relationships between the portions of the brain data 252. The inverted encoder subnetwork 270 can then process the embeddings 262 to generate reconstructed brain data 272 that identifies changes in one or more particular portions of the brain data (i.e., local changes) that can influence the rest of the brain data such that the brain data reflects the desired characteristics of the input brain data 252. Furthermore, typically the differences between the brain data of different patients are continuous and relatively standard, e.g., the values of a particular element of brain data corresponding to respective patients can fall within a limited range. Therefore, the reconstructed brain data 272 generated by the inverted autoencoder neural network 250 can identify standard values for most elements (i.e., elements that would not have influence on the desired characteristics of the input brain data 252), while identifying relatively abnormal values (corresponding to the local effects of the future treatment) for the elements that would actualize the particular characteristics of the input brain data 252.

In some implementations, the inverted autoencoder neural network system 250 can generate multiple different sets of reconstructed desired brain data 272 from a single set of desired brain data 252. Because there is some loss of information when the autoencoder neural network system 200 generates the embedding 212 for a particular set of brain data 202, multiple different sets of brain data 202 can correspond to a single set of reconstructed brain data 222. Thus, the inverted autoencoder neural network system 250 can determine multiple different sets of reconstructed desired brain data 272 that, if processed by the autoencoder neural network system 200, would generate the same set of desired brain data 252.

After the inverted autoencoder neural network system 250 has generated the multiple different sets of reconstructed desired brain data 272, an external system can select a particular set from the multiple different sets of reconstructed desired brain data 272 from which to determine the parameters of the future treatment. For example, the external system can determine, for each of the multiple different sets, a difference between i) the set of reconstructed desired brain data 272 and ii) the current brain data of the patient. The external system can then select the particular set from the multiple different sets according to the respective determined differences. As a particular example, the external system can select the particular set that has a smallest difference from the current brain data of the patient, i.e., the particular set of reconstructed desired brain data 272 that reflects the smallest local effect that would induce the desired global effect and thus that may correspond to the least intensive treatment. As another particular example, the external system can select the particular set that has the most localized differences from the current brain data of the patient, i.e., a particular set of reconstructed desired brain data 272 from which a treatment can be determined that can target a single location in the brain of the patient instead of multiple different locations.

In some other implementations, a system can generate reconstructed desired brain data 272 by processing desired brain data 252 using a generative neural network that has been trained adversarially. For example, the generative neural network can process the desired brain data 252 using one or more feedforward neural network layers to generate the reconstructed brain data 272.

A training system can train the generative neural network using a generative adversarial network that includes the generative neural network and one or more discriminator neural networks. The discriminator neural networks are each configured to process the output of the generative neural network (in this example, a set of reconstructed desired brain data 272) and to generate a prediction of whether the reconstructed desired brain data 272 is real or synthetic, i.e., whether the reconstructed desired brain data 272 has is (or has been generated from) real brain data of a patient (e.g., real fMRI data that has been captured from the brain of the patient) or whether the reconstructed desired brain data 272 has been generated by the generative neural network. Generally, the training system determines the updates to the parameters of the generative neural network in order to increase an error in the respective predictions of the discriminator neural networks, and determines updates to the parameters of the discriminator neural networks in order to decrease their errors. Example generative adversarial networks are discussed in more detail in the U.S. Patent Application entitled "Predicting Brain Data using Machine Learning Models," to Michael Sughrue, Stephane Doyen, and Peter Nicholas, filed on the same day as the present application and incorporated herein by reference in its entirety.

Figure 3:
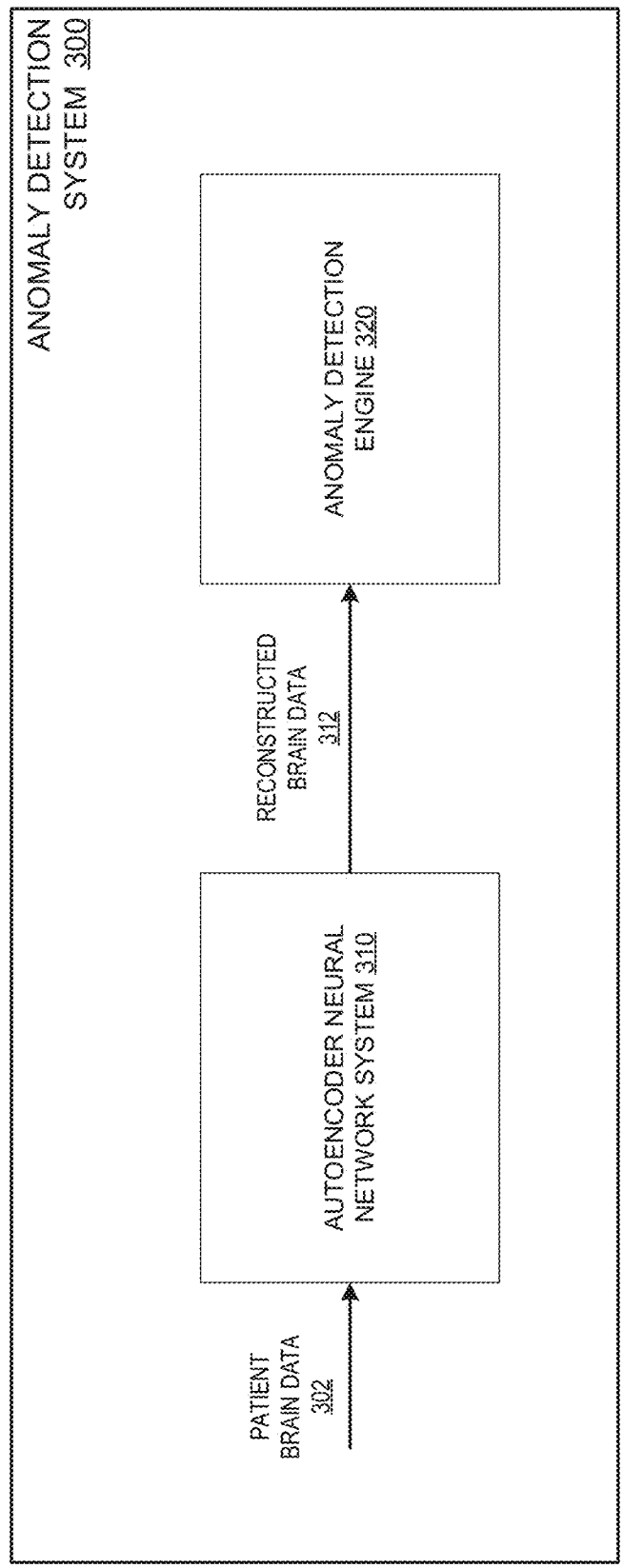
FIG. 3 is a diagram of an example anomaly detection system.

FIG. 3 is a diagram of an example anomaly detection system 300. The anomaly detection system 300 is an example of systems implemented as computer programs on one or more computers in one or more locations, in which the systems, components, and techniques described below can be implemented.

The anomaly detection system 300 is configured to detect anomalies in brain data 302 characterizing the brain of a patient. As described above, the brain data 302 can include any data characterizing the brain of the patient. For example, the brain data 302 can include correlation data that characterizes, for each pair of parcellations in the brain of the patient, a degree of correlation between the respective brain activity of the parcellations. As another example, the brain data 302 can include tractography data that characterizes neural tracts connecting pairs of parcellations in the brain of the patient.

The anomaly detection system includes an autoencoder neural network system 310 and an anomaly detection system 320. The autoencoder neural network system is configured to process the brain data 302 and to generate reconstructed brain data 312. For example, the autoencoder neural network system 310 can be the autoencoder neural network system 200 described above with reference to FIG. 2A.

The anomaly detection engine 320 is configured to process the reconstructed brain data 312, and optionally the patient brain data 302, to determine whether the brain data 302 or 312 is anomalous, i.e., outside of a range of normal values or otherwise dissimilar with typical brain data of patients.

In some implementations, the patient brain data 302 is real brain data captured from the brain of the patient (or generated from real brain data captured from the brain of the patient), and the anomaly detection engine 320 processes i) the patient brain data 302 and ii) the reconstructed brain data 312 to determine whether the patient brain data 302 is anomalous. In particular, the anomaly detection engine 320 can determine whether the patient brain data 302 is anomalous according to a difference between the patient brain data 302 and the reconstructed brain data 312.

For example, the anomaly detection engine 320 can determine the difference to be the $L_1$ or $L_2$ distance between the brain data 302 and the reconstructed brain data 312, or squared versions thereof.

In some implementations, the anomaly detection engine 320 can determine that the patient brain data 302 is anomalous if the determined difference between the patient brain data 302 and the reconstructed brain data 312 exceeds a predetermined threshold. The predetermined threshold can be determined during or after training of the autoencoder neural network system 310. For example, after a training system has trained the autoencoder neural network system 310, the training system can process multiple testing examples corresponding to respective different patients using the autoencoder neural network system 310, and determine, for each training example, the difference between the input brain data and the reconstructed brain data. The training system can then determine the predetermined threshold such that the computed difference for some percentage of the testing examples, e.g., 0.8, 0.9, 0.95, or 0.99, are below the threshold while the computed difference for the remaining testing examples are above the threshold.

The autoencoder neural network system 310 has been trained to generate reconstructed brain data 312 that is similar to the patient brain data 302, using training example that include "normal" brain data, i.e., brain data that is not anomalous, corresponding to respective different patients. Therefore, if the anomaly detection engine 320 determines that the reconstructed brain data 312 is dissimilar to the patient brain data 302, according to the difference between the two, then the anomaly detection engine 320 can determine that the patient brain data 302 is anomalous.

In some other implementations, the patient brain data 302 is modified brain data that characterizes a predicted local effect of a future treatment on the brain of the patient, as described above with reference to FIG. 2A. The anomaly detection engine can process the corresponding reconstructed brain data 312, which characterizes a predicted global effect of the future treatment on the brain of the patient, to determine whether the reconstructed brain data 312 is anomalous. That is, the anomaly detection engine 320 can determine whether providing the future treatment to the patient might cause one or more anomalies in the brain of the patient, which might indicate that the treatment may be dangerous for the patient. In other words, when a clinician is considering a treatment for a patient, the clinician or another user can modify the patient's brain data to include the predicted change as a result of the proposed treatment, producing patient-specific modified brain data. The system can then i) apply the autoencoder to the patient-specific modified brain data to produce reconstructed brain data, and ii) detect potential anomalies in the reconstructed brain data (e.g., using any of a variety of anomaly detection techniques).

In some such implementations, the anomaly detection engine 320 can process the reconstructed brain data 312 using a machine learning model that is configured to process reconstructed brain data 312 to determine whether it is anomalous. For example, the machine learning model generates a prediction characterizing a likelihood that the reconstructed brain data 312 is anomalous, e.g., a scalar value between 0 and 1. As another example, the machine learning model identifies one or more elements in the reconstructed brain data 312 that are anomalous. The machine learning model can be trained using brain data (e.g., real brain data and/or reconstructed brain data) corresponding to multiple different patients.

In some other such implementations, the anomaly detection engine 320 can determine whether the reconstructed brain data 312 is anomalous if the reconstructed brain data 312 is outside of a "normal" range of values as defined by a set of brain data corresponding to other patients. For example, the anomaly detection engine 320 can obtain "normal" brain data that identifies, for each of one or more elements in the reconstructed brain data 312, a range of values for the element that is considered normal. The normal brain data can be determined from brain data captured from hundreds, thousands, or millions of other patients. As a particular example, the normal brain data can identify, for each element in the reconstructed brain data 312, an average value and a standard deviation of values, as determined from the brain data of the other patients.

The anomaly detection engine 320 can use the normal brain data to identify one or more elements of the reconstructed brain data 312 that are anomalous. As a particular example, the anomaly detection engine 320 might determine that the value of a particular element is anomalous if the value is outside a range defined by the average value and standard deviation of values. For example, the value of an element can be determine to be anomalous if it is outside one, two, three, or four standard deviations of the average value.

The anomaly detection engine 320 can then determine whether the one or more determined anomalous elements in the reconstructed brain data 312 indicate that the future treatment may be unsafe. For example, the anomaly detection system can obtain data identifying one or more particular elements in the reconstructed brain data 312 that, if they are determined to be anomalous, indicate an issue in the brain of the patient and therefore that the future treatment may be unsafe.

In some implementations, the anomaly detection system 300 can provide data representing the one or more identified anomalous elements in the reconstructed brain data 312 to a downstream system for further processing. For example, the anomaly detection system 300 can provide data to a graphical user interface for displaying data representing the one or more anomalous elements to a user. As another example, the anomaly detection system 300 can provide data to a machine learning system that is configured to process a model input that includes the data and generate a model output that is clinically relevant for a user. For example, a machine learning model can process the data to generate a prediction for whether the patient has a particular brain disease, e.g., autism, depression, or schizophrenia.

Anomaly detection systems are described in more detail in U.S. patent application Ser. No. 16/920,078, filed on Jul. 2, 2020, the contents of which are hereby incorporated by reference in their entirety.

Figure 4:
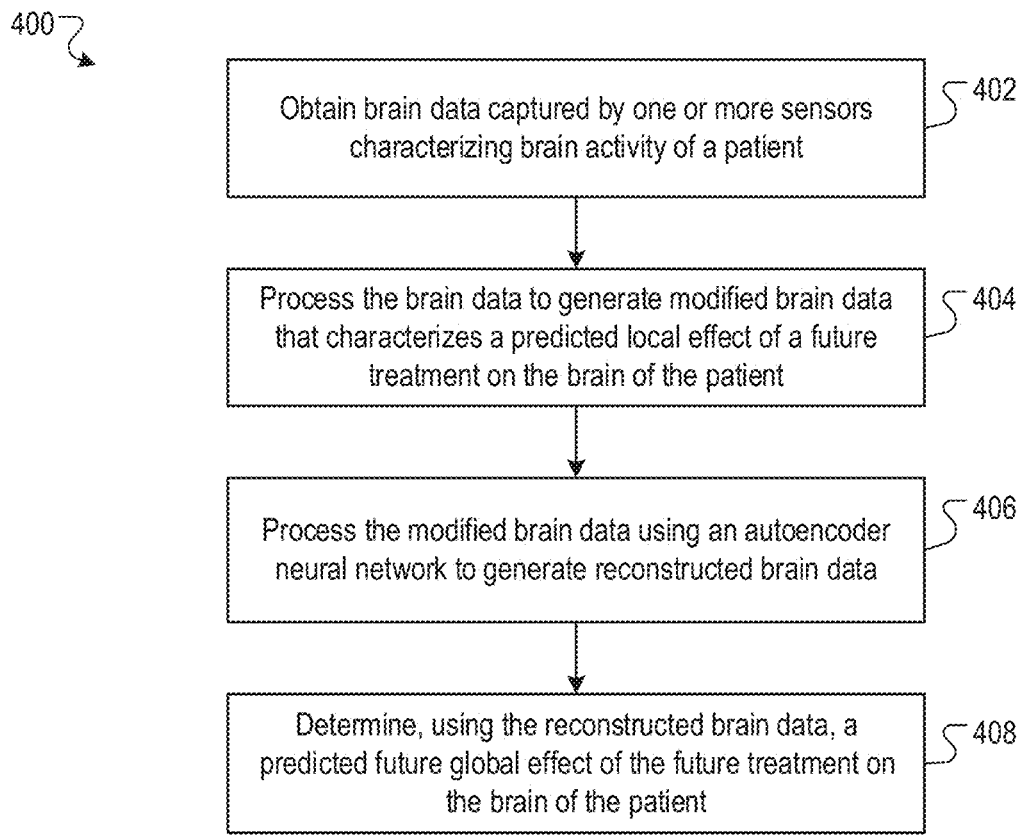
FIG. 4 is a flowchart of an example process for processing brain data using an autoencoder neural network.

FIG. 4 is a flowchart of an example process 400 for processing brain data using an autoencoder neural network. The process 400 can be implemented by one or more computer programs installed on one or more computers and programmed in accordance with this specification. For example, the process 400 can be performed by the computer server module depicted in FIG. 1A. For convenience, the process 400 will be described as being performed by a system of one or more computers.

The system obtains brain data captured from one or more sensors characterizing brain activity of a patient (step 402).

The system processes the brain data to generate modified brain data that characterizes a predicted local effect of a future treatment on the brain of the patient (step 404). For example, the system can determine the target location of the future treatment in the brain of the patient, identify one or more elements of the brain data corresponding to the target location, and modify values of the one or more elements according to one or more parameters of the future treatment.

The system processes the modified brain data using an autoencoder neural network to generate reconstructed brain data (step 406). The system can process a network input that includes the modified brain data using an encoder subnetwork of the autoencoder neural network to generate an embedding of the network input, and then process the embedding of the network input using a decoder subnetwork of the autoencoder neural network to generate the reconstructed brain data.

The system determines, using the reconstructed brain data, a predicted future global effect of the future treatment on the brain of the patient (step 408). For example, the system can process the reconstructed brain data to identify one or more anomalies in the reconstructed brain data. The identified anomalies might indicate that the future treatment is unsafe. As a particular example, the system can obtain normal brain data that identifies, for each of one or more elements in the reconstructed brain data, a respective normal range of values for the element. The system can then compare i) the reconstructed brain data and ii) the normal brain data to identify the one or more anomalies.

In some implementations, the system performs the process 400 multiple times for respective different future treatments. The system can then select a particular future treatment form the multiple different future treatments using the respective predicted global effects of the multiple future treatments. For example, the system can select the particular future treatment that has a global effect that reflects the safest and most effective outcome of the multiple different future treatments.

Figure 5:
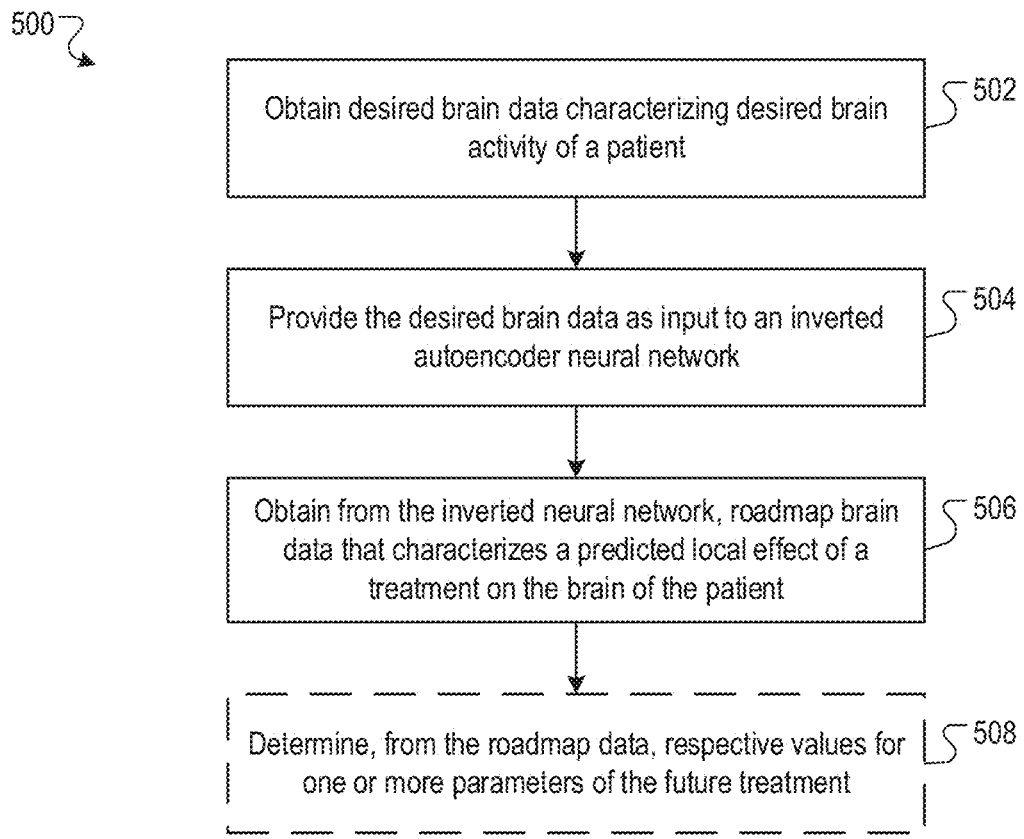
FIG. 5 is a flowchart of an example process for processing brain data using an inverted autoencoder neural network.

FIG. 5 is a flowchart of an example process 500 for processing brain data using an inverted autoencoder neural network. The process 500 can be implemented by one or more computer programs installed on one or more computers and programmed in accordance with this specification. For example, the process 500 can be performed by the computer server module depicted in FIG. 1A. For convenience, the process 500 will be described as being performed by a system of one or more computers.

The system obtains desired brain data characterizing desired brain activity of a patient (step 502). The desired brain data can characterize a possible global effect of a future treatment on the brain of the patient. For example, the desired brain data can be the same as (or generated from) brain data of a second patient that characterizes the desired brain activity.

The system provides the desired brain data as input to an inverted autoencoder neural network (step 504). The inverted autoencoder neural network can be determined using a trained autoencoder neural network, including inverting one or more operations of the autoencoder neural network.

The autoencoder can be configured to process brain data of a patient and to generate reconstructed brain data of the patient by i) processing a network input that includes the brain data using an encoder subnetwork to generate an embedding of the network input, and ii) processing the embedding of the network input using a decoder subnetwork to generate the reconstructed brain data.

The system obtains, from the inverted neural network, roadmap brain data that characterizes a predicted local effect of the future treatment on the brain of the patient (step 506).

Optionally, the system can determine, from the roadmap data, respective values for one or more parameters of the future treatment (step 508). The values for the one or more parameters can be determined such that the future treatment actualizes the desired brain activity of the patient.

In some implementations, the system can obtain, from the inverted neural network, multiple different sets of roadmap data that each characterize a predicted local effect of the future treatment if the future treatment were to be provided to the patient according to respective different values for one or more parameters of the future treatment. The system can then select particular values for the one or more parameters of the future treatment using the respective sets of roadmap data.

Figure 6:
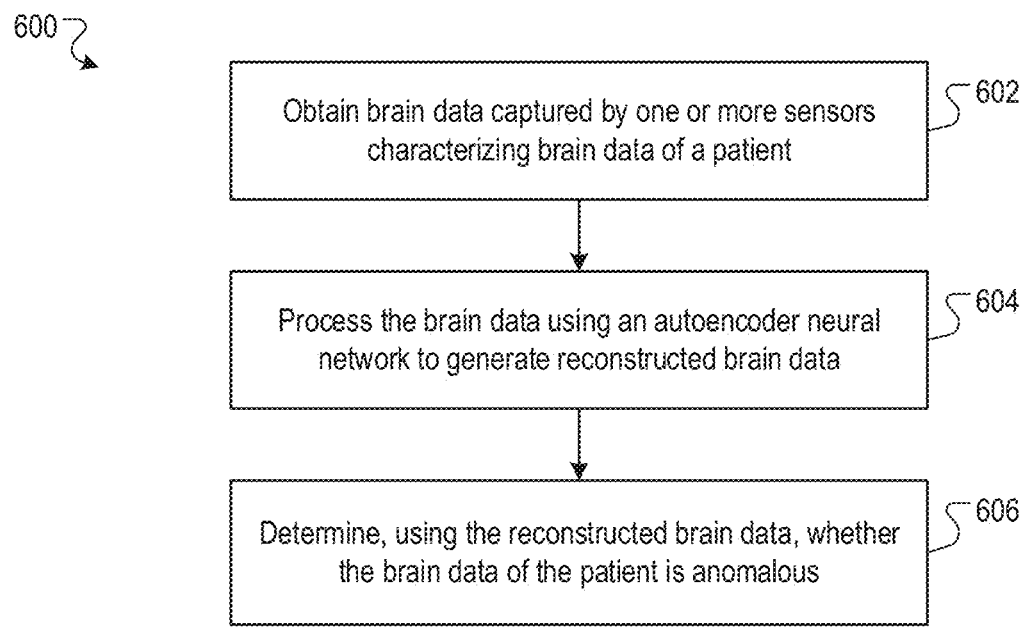
FIG. 6 is a flowchart of an example process for identifying anomalous brain data using an autoencoder neural network.

FIG. 6 is a flowchart of an example process 600 for identifying anomalous brain data using an autoencoder neural network. The process 600 can be implemented by one or more computer programs installed on one or more computers and programmed in accordance with this specification. For example, the process 600 can be performed by the computer server module depicted in FIG. 1A. For convenience, the process 600 will be described as being performed by a system of one or more computers.

The system obtains brain data captured from one or more sensors characterizing brain activity of a patient (step 602).

The system processes the brain data using an autoencoder neural network to generate reconstructed brain data (step 604). The system can process a network input that includes the brain data using an encoder subnetwork of the autoencoder neural network to generate an embedding of the network input, and then process the embedding of the network input using a decoder subnetwork of the autoencoder neural network to generate the reconstructed brain data.

The system determines, using the reconstructed brain data, whether the brain data of the patient is anomalous (step 606). For example, the system can determine an error between the brain data and the reconstructed brain data, and determine whether the error satisfies a predetermine threshold. The predetermined threshold can be determined according to training errors, where each training error represents an error between i) second brain data of a second patient, and ii) second reconstructed brain data generated by processing the second brain data using the autoencoder neural network.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g, a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network.

Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a method comprising:
obtaining brain data captured by one or more sensors characterizing brain activity of a patient;
processing the brain data to generate modified brain data that characterizes a predicted local effect of a future treatment on the brain of the patient, wherein the local effect of the future treatment is an effect of the future treatment on a region of the brain that is local to a target location of the future treatment in the brain;
processing the modified brain data using an autoencoder neural network to generate reconstructed brain data, wherein:
 the processing comprises:
  processing a network input comprising the modified brain data using an encoder subnetwork to generate an embedding of the network input, and
  processing the embedding of the network input using a decoder subnetwork to generate the reconstructed brain data; and
 the autoencoder neural network has been trained by, at each of a plurality of training time steps:
  processing, according to current values of a plurality of network parameters of the autoencoder neural network, a training network input comprising second brain data of a second patient to generate reconstructed second brain data, and
  determining an update to the current values of the plurality of network parameters according to an error between i) the second brain data and ii) the reconstructed second brain data; and
determining, using the reconstructed brain data, a predicted global effect of the future treatment on the brain of the patient, wherein the global effect of the future treatment is an effect of the future treatment on one or more regions of the brain that are not local to the target of the future treatment in the brain.

Embodiment 2 is the method of embodiment 1, wherein processing the brain data to generate modified brain data that characterizes a predicted local effect of a treatment on the brain of the patient comprises:
determining the target location of the future treatment in the brain of the patient;
identifying one or more elements of the brain data corresponding to the target location; and
modifying values of the one or more elements according to one or more parameters of the future treatment.

Embodiment 3 is the method of any one of embodiments 1 or 2, wherein determining the predicted global effect of the future treatment comprises processing the reconstructed brain data to identify one or more anomalies in the reconstructed brain data.

Embodiment 4 is the method of embodiment 3, wherein identifying one or more anomalies in the reconstructed brain data comprises:
obtaining normal brain data identifying, for each of one or more elements in the reconstructed brain data, a respective normal range of values for the element; and
comparing i) the reconstructed brain data and ii) the normal brain data to identify the one or more anomalies.

Embodiment 5 is the method of any one of embodiments 1-4, further comprising:
for each of one or more second future treatments:
 processing the brain data to generate second modified brain data that characterizes a predicted local effect of the second future treatment on the brain of the patient;
 processing the second modified brain data using the autoencoder neural network to generate second reconstructed brain data; and
 determining, using the second reconstructed brain data, a predicted global effect of the second future treatment on the brain of the patient; and
selecting, using the respective predicted global effects of the future treatment and the one or more second future treatments, a particular future treatment.

Embodiment 6 is the method of any one of embodiments 1-5, wherein the future treatment is a transcranial magnetic stimulation (TMS) treatment.

Embodiment 7 is the method of any one of embodiments 1-6, wherein:
the brain data comprises correlation data characterizing, for each of a plurality of pairs of parcellations formed from a set of parcellations in the brain of the patient, where each pair comprises a first parcellation and a second parcellation, a degree of correlation between the brain activity of the first parcellation and the brain activity of the second parcellation in the brain of the patient.

Embodiment 8 is a method comprising:
obtaining desired brain data characterizing desired brain activity of a patient, wherein the desired brain data characterizes a possible global effect of a future treatment on the brain of the patient, wherein the global effect of the treatment is an effect of the treatment on one or more regions of the brain that are not local to a target of the treatment in the brain;
providing the desired brain data as input to an inverted autoencoder neural network, wherein:
 the inverted autoencoder neural network has been determined using a trained autoencoder neural network, the determining comprising inverting a plurality of operations of the autoencoder neural network;
 the autoencoder neural network is configured to process brain data of a patient and to generate reconstructed brain data of the patient, the processing comprising:
  processing a network input comprising the brain data using an encoder subnetwork to generate an embedding of the network input, and
  processing the embedding of the network input using a decoder subnetwork to generate the reconstructed brain data; and
 the autoencoder neural network has been trained by, at each of a plurality of training time steps:
  processing, according to current values of a plurality of network parameters of the autoencoder neural network, a training network input comprising second brain data of a second patient to generate reconstructed second brain data, and determining an update to the current values of the plurality of network parameters according to an error between i) the second brain data and ii) the reconstructed second brain data; and obtaining, from the inverted autoencoder neural network, roadmap brain data that characterizes a predicted local effect of the future treatment on the brain of the patient, wherein the local effect of the future treatment is an effect of the future treatment on a region of the brain that is local to the target of the treatment.

Embodiment 9 is the method of embodiment 8, further comprising:

determining, from the roadmap brain data, respective values for one or more parameters of the future treatment in order to actualize the desired brain activity of the patient.

Embodiment 10 is the method of embodiment 9, wherein the parameters of the future treatment comprise one or more of:

a recommended target location of the feature treatment, a recommended strength of the future treatment, a recommended dose of the future treatment; or a recommended schedule of the future treatment.

Embodiment 11 is the method of any one of embodiments 8-10, wherein obtaining desired brain data characterizing desired brain activity of a patient comprises obtaining brain data of a second patient that characterizes the desired brain activity.

Embodiment 12 is the method of any one of embodiments 8-11, wherein:

the roadmap data characterizes a predicted local effect of the future treatment on the brain of the patient if the future treatment were provided according to first values for one or more parameters of the future treatment; and the method further comprises:

obtaining, from the inverted autoencoder neural network, one or more sets of second roadmap brain data that each characterize a predicted local effect of the future treatment on the brain of the patient if the future treatment were provided according to respective second values of the one or more parameters of the future treatment; and selecting particular values for the one or more parameters of the future treatment using the roadmap brain data and the one or more sets of second roadmap data.

Embodiment 13 is the method of any one of embodiments 8-12, wherein the future treatment is a transcranial magnetic stimulation (TMS) treatment.

Embodiment 14 is the method of any one of embodiments 8-13, wherein:

the brain data comprises correlation data characterizing, for each of a plurality of pairs of parcellations formed from a set of parcellations in the brain of the patient, where each pair comprises a first parcellation and a second parcellation, a degree of correlation between the brain activity of the first parcellation and the brain activity of the second parcellation in the brain of the patient.

Embodiment 15 is a method comprising:

obtaining brain data generated from data captured by one or more sensors characterizing brain activity of a patient;

processing the brain data using an autoencoder neural network to generate reconstructed brain data, wherein:

the processing comprises:

processing a network input comprising the brain data using an encoder subnetwork to generate an embedding of the network input, and processing the embedding of the network input using a decoder subnetwork to generate the reconstructed brain data; and the autoencoder neural network has been trained by, at each of a plurality of training time steps:

processing, according to current values of a plurality of network parameters of the autoencoder neural network, a training network input comprising second brain data of a second patient to generate reconstructed second brain data, and determining an update to the current values of the plurality of network parameters according to an error between i) the second brain data and ii) the reconstructed second brain data; and determining, using the reconstructed brain data, whether the brain data of the patient is anomalous.

Embodiment 16 is the method of embodiment 15, wherein determining whether the brain data of the patient is anomalous comprises:

determining an error between the brain data and the reconstructed brain data; and determining whether the error satisfies a predetermined threshold.

Embodiment 17 is the method of embodiment 16, wherein the threshold is determined according to a plurality of training errors, wherein each training error represents an error between i) second brain data of a second patient, and ii) second reconstructed brain data generated by processing the second brain data using the autoencoder neural network.

Embodiment 18 is the method of any one of embodiments 15-17, wherein:

the brain data comprises correlation data characterizing, for each of a plurality of pairs of parcellations formed from a set of parcellations in the brain of the patient, where each pair comprises a first parcellation and a second parcellation, a degree of correlation between the brain activity of the first parcellation and the brain activity of the second parcellation in the brain of the patient.

Embodiment 19 is the method of any one of embodiments 15-18, wherein the brain data is modified brain data that characterizes a predicted local effect of a future treatment on the brain of the patient, wherein the local effect of the future treatment is an effect of the future treatment on a region of the brain that is local to a target location of the future treatment in the brain.

Embodiment 20 is the method of embodiment 19, wherein determining whether the brain data of the patient is anomalous comprises:

obtaining normal brain data identifying, for each of one or more particular elements of the brain data of the patient, a respective normal range of values for the particular element; and comparing i) the reconstructed brain data and ii) the normal brain data to identify the one or more possible anomalies.

Embodiment 21 is the method of embodiment 20, wherein:

the normal brain data is generated from a plurality of sets of brain data corresponding to respective other patients;

the normal brain data comprises, for each of the one or more particular elements of the brain data of the patient, data characterizing i) a measure of central tendency of the value of the particular element and ii) a measure of variance of the value of the particular element, wherein the measure of central tendency and the measure of variance have been computed using the plurality of sets of brain data; and for each of the one or more particular elements of the brain data of the patient, the normal range of values for the particular element is defined by a maximum value and a minimum value, wherein the maximum value and the minimum value are linear combinations of the corresponding measure of central tendency of the particular element and the corresponding measure of variance of the particular element.

Embodiment 22 is a system comprising one or more computers and one or more storage devices storing instructions that are operable, when executed by the one or more computers, to cause the one or more computers to perform the method of any one of embodiments 1-21.

Embodiment 23 is one or more non-transitory computer storage medium encoded with a computer program, the program comprising instructions that are operable, when executed by data processing apparatus, to cause the data processing apparatus to perform the method of any one of embodiments 1-21.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain some cases, multitasking and parallel processing may be advantageous.

What is claimed is:

1. A method comprising:
   obtaining brain data captured by one or more sensors characterizing brain activity of a patient;
   processing the brain data to generate modified brain data that characterizes a predicted local effect of a future treatment on the brain of the patient, wherein the predicted local effect is a prediction of an effect of the future treatment on a region of the brain that is local to a target location of the future treatment in the brain;
   processing the modified brain data using an autoencoder neural network to generate reconstructed brain data, wherein:
       the processing comprises:
           processing a network input generated from the modified brain data using an encoder subnetwork to generate an embedding of the network input, and
           processing the embedding of the network input using a decoder subnetwork to generate the reconstructed brain data; and
       the autoencoder neural network has been configured through training to process the network input and to generate reconstructed brain data that characterizes a predicted global effect of the future treatment on the brain of the patient, wherein the predicted global effect is a prediction of an effect of the future treatment on at least one or more regions of the brain that are not local to the target location of the future treatment in the brain, the training comprising, at each of a plurality of training time steps:
           obtaining second brain data captured by one or more second sensors characterizing brain activity of a second patient;
           generating, from the obtained second brain data, a training network input;
           processing, according to current values of a plurality of network parameters of the autoencoder neural network, the training network input to generate reconstructed second brain data, and
           determining an update to the current values of the plurality of network parameters according to an error between i) the second brain data and ii) the reconstructed second brain data; and
   determining, using the reconstructed brain data, the predicted global effect of the future treatment on the brain of the patient.

2. The method of claim 1, wherein processing the brain data to generate modified brain data that characterizes a predicted local effect of a treatment on the brain of the patient comprises:
   determining the target location of the future treatment in the brain of the patient;
   identifying one or more elements of the brain data corresponding to the target location; and
   modifying values of the one or more elements according to one or more parameters of the future treatment.

3. The method of claim 1, wherein determining the predicted global effect of the future treatment comprises processing the reconstructed brain data to identify one or more anomalies in the reconstructed brain data.

4. The method of claim 3, wherein identifying one or more anomalies in the reconstructed brain data comprises:
   obtaining normal brain data identifying, for each of one or more elements in the reconstructed brain data, a respective normal range of values for the element; and
   comparing i) the reconstructed brain data and ii) the normal brain data to identify the one or more anomalies.

5. The method of claim 1, further comprising:
for each of one or more second future treatments:
   processing the brain data to generate second modified brain data that characterizes a predicted local effect of the second future treatment on the brain of the patient;

processing the second modified brain data using the autoencoder neural network to generate second reconstructed brain data; and determining, using the second reconstructed brain data, a predicted global effect of the second future treatment on the brain of the patient; and selecting, using the respective predicted global effects of the future treatment and the one or more second future treatments, a particular future treatment.

6. The method of claim 1, wherein the future treatment is a transcranial magnetic stimulation (TMS) treatment.

7. The method of claim 1, wherein:

the brain data comprises correlation data characterizing, for each of a plurality of pairs of parcellations formed from a set of parcellations in the brain of the patient, where each pair comprises a first parcellation and a second parcellation, a degree of correlation between the brain activity of the first parcellation and the brain activity of the second parcellation in the brain of the patient.

8. A system comprising one or more computers and one or more storage devices storing instructions that are operable, when executed by the one or more computers, to cause the one or more computers to perform operations comprising:

obtaining brain data captured by one or more sensors characterizing brain activity of a patient;

processing the brain data to generate modified brain data that characterizes a predicted local effect of a future treatment on the brain of the patient, wherein the predicted local effect is a prediction of an effect of the future treatment on a region of the brain that is local to a target location of the future treatment in the brain;

processing the modified brain data using an autoencoder neural network to generate reconstructed brain data, wherein:

the processing comprises:

processing a network input generated from the modified brain data using an encoder subnetwork to generate an embedding of the network input, and processing the embedding of the network input using a decoder subnetwork to generate the reconstructed brain data; and the autoencoder neural network has been configured through training to process the network input and to generate reconstructed brain data that characterizes a predicted global effect of the future treatment on the brain of the patient, wherein the predicted global effect is a prediction of an effect of the future treatment on at least one or more regions of the brain that are not local to the target location of the future treatment in the brain, the training comprising, at each of a plurality of training time steps:

obtaining second brain data captured by one or more second sensors characterizing brain activity of a second patient;

generating, from the obtained second brain data, a training network input;

processing, according to current values of a plurality of network parameters of the autoencoder neural network, the training network input to generate reconstructed second brain data, and determining an update to the current values of the plurality of network parameters according to an error between i) the second brain data and ii) the reconstructed second brain data; and determining, using the reconstructed brain data, the predicted global effect of the future treatment on the brain of the patient.

9. The system of claim 8, wherein processing the brain data to generate modified brain data that characterizes a predicted local effect of a treatment on the brain of the patient comprises:

determining the target location of the future treatment in the brain of the patient;

identifying one or more elements of the brain data corresponding to the target location; and modifying values of the one or more elements according to one or more parameters of the future treatment.

10. The system of claim 8, wherein determining the predicted global effect of the future treatment comprises processing the reconstructed brain data to identify one or more anomalies in the reconstructed brain data.

11. The system of claim 10, wherein identifying one or more anomalies in the reconstructed brain data comprises:

obtaining normal brain data identifying, for each of one or more elements in the reconstructed brain data, a respective normal range of values for the element; and comparing i) the reconstructed brain data and ii) the normal brain data to identify the one or more anomalies.

12. The system of claim 8, the operations further comprising:

for each of one or more second future treatments:

processing the brain data to generate second modified brain data that characterizes a predicted local effect of the second future treatment on the brain of the patient;

processing the second modified brain data using the autoencoder neural network to generate second reconstructed brain data; and determining, using the second reconstructed brain data, a predicted global effect of the second future treatment on the brain of the patient; and selecting, using the respective predicted global effects of the future treatment and the one or more second future treatments, a particular future treatment.

13. The system of claim 8, wherein the future treatment is a transcranial magnetic stimulation (TMS) treatment.

14. The system of claim 8, wherein:

the brain data comprises correlation data characterizing, for each of a plurality of pairs of parcellations formed from a set of parcellations in the brain of the patient, where each pair comprises a first parcellation and a second parcellation, a degree of correlation between the brain activity of the first parcellation and the brain activity of the second parcellation in the brain of the patient.

15. One or more non-transitory storage media storing instructions that when executed by one or more computers cause the one or more computers to perform operations comprising:

obtaining brain data captured by one or more sensors characterizing brain activity of a patient;

processing the brain data to generate modified brain data that characterizes a predicted local effect of a future treatment on the brain of the patient, wherein the predicted local effect is a prediction of an effect of the future treatment on a region of the brain that is local to a target location of the future treatment in the brain;

processing the modified brain data using an autoencoder neural network to generate reconstructed brain data, wherein:

the processing comprises:
  processing a network input generated from the modified brain data using an encoder subnetwork to generate an embedding of the network input, and
  processing the embedding of the network input using a decoder subnetwork to generate the reconstructed brain data; and
the autoencoder neural network has been configured through training to process the network input and to generate reconstructed brain data that characterizes a predicted global effect of the future treatment on the brain of the patient, wherein the predicted global effect is a prediction of an effect of the future treatment on at least one or more regions of the brain that are not local to the target location of the future treatment in the brain, the training comprising, at each of a plurality of training time steps:
  obtaining second brain data captured by one or more second sensors characterizing brain activity of a second patient;
  generating, from the obtained second brain data, a training network input;
  processing, according to current values of a plurality of network parameters of the autoencoder neural network, the training network input to generate reconstructed second brain data, and
  determining an update to the current values of the plurality of network parameters according to an error between i) the second brain data and ii) the reconstructed second brain data; and
determining, using the reconstructed brain data, the predicted global effect of the future treatment on the brain of the patient.

16. The non-transitory storage media of claim 15, wherein processing the brain data to generate modified brain data that characterizes a predicted local effect of a treatment on the brain of the patient comprises:
  determining the target location of the future treatment in the brain of the patient;
  identifying one or more elements of the brain data corresponding to the target location; and
  modifying values of the one or more elements according to one or more parameters of the future treatment.

17. The non-transitory storage media of claim 15, wherein determining the predicted global effect of the future treatment comprises processing the reconstructed brain data to identify one or more anomalies in the reconstructed brain data.

18. The non-transitory storage media of claim 17, wherein identifying one or more anomalies in the reconstructed brain data comprises:
  obtaining normal brain data identifying, for each of one or more elements in the reconstructed brain data, a respective normal range of values for the element; and
  comparing i) the reconstructed brain data and ii) the normal brain data to identify the one or more anomalies.

19. The non-transitory storage media of claim 15, the operations further comprising:
  for each of one or more second future treatments:
    processing the brain data to generate second modified brain data that characterizes a predicted local effect of the second future treatment on the brain of the patient;
    processing the second modified brain data using the autoencoder neural network to generate second reconstructed brain data; and
    determining, using the second reconstructed brain data, a predicted global effect of the second future treatment on the brain of the patient; and
  selecting, using the respective predicted global effects of the future treatment and the one or more second future treatments, a particular future treatment.

20. The non-transitory storage media of claim 15, wherein:
  the brain data comprises correlation data characterizing, for each of a plurality of pairs of parcellations formed from a set of parcellations in the brain of the patient, where each pair comprises a first parcellation and a second parcellation, a degree of correlation between the brain activity of the first parcellation and the brain activity of the second parcellation in the brain of the patient.

* * * * *